United States Patent
Rabiner et al.

(10) Patent No.: US 6,802,835 B2
(45) Date of Patent: Oct. 12, 2004

(54) APPARATUS AND METHOD FOR USING A STEERABLE CATHETER DEVICE

(75) Inventors: Robert A. Rabiner, North Reading, MA (US); Daniel E. Rabiner, North Reading, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

(21) Appl. No.: 10/732,869

(22) Filed: Dec. 10, 2003

(65) Prior Publication Data

US 2004/0122417 A1 Jun. 24, 2004

Related U.S. Application Data

(63) Continuation of application No. 10/462,182, filed on Jun. 16, 2003, now Pat. No. 6,679,873, which is a continuation of application No. 09/665,328, filed on Sep. 19, 2000, now Pat. No. 6,579,279.
(60) Provisional application No. 60/156,051, filed on Sep. 24, 1999.

(51) Int. Cl.⁷ .......................................... A61M 25/098
(52) U.S. Cl. ..................................... 604/528; 604/529
(58) Field of Search .............................. 604/528, 529, 604/95.02, 95.03, 95.04, 7, 22, 52, 174, 164.1, 531; 606/41, 49; 609/122; 600/374, 381, 393, 585

(56) References Cited

U.S. PATENT DOCUMENTS

| | | | |
|---|---|---|---|
| 4,601,705 A | 7/1986 | McCoy | 604/95 |
| 4,738,666 A | 4/1988 | Fuqua | 604/280 |
| 4,758,222 A | 7/1988 | McCoy | 604/95 |
| 4,846,174 A * | 7/1989 | Willard et al. | 606/194 |
| 4,917,104 A * | 4/1990 | Rebell | 600/585 |
| 5,055,101 A | 10/1991 | McCoy | 604/95 |
| 5,123,903 A | 6/1992 | Quaid et al. | 604/22 |
| 5,152,748 A | 10/1992 | Chastagner | 604/95 |
| 5,315,996 A | 5/1994 | Lundquist | 604/374 |
| 5,571,085 A * | 11/1996 | Accisano, III | 604/95.01 |
| 5,843,017 A | 12/1998 | Yoon | 604/22 |
| 6,017,340 A * | 1/2000 | Cassidy et al. | 606/47 |
| 6,146,381 A | 11/2000 | Bowe et al. | 606/41 |
| 6,156,018 A | 12/2000 | Hassett | 604/281 |
| 6,190,353 B1 | 2/2001 | Makower et al. | 604/95.01 |
| 6,200,315 B1 | 3/2001 | Gaiser et al. | 606/41 |
| 6,231,518 B1 * | 5/2001 | Grabek et al. | 600/508 |
| 6,283,951 B1 | 9/2001 | Flaherty et al. | 604/529 |
| 6,309,379 B1 | 10/2001 | Willard et al. | 600/467 |

* cited by examiner

*Primary Examiner*—Quang T. Van
(74) *Attorney, Agent, or Firm*—Palmer & Dodge, LLP; Richard B. Smith; David J. Dykeman

(57) ABSTRACT

A handle includes a body portion and a handle portion which is slidably and rotatably mounted on the body portion. Shoulders on the body portion and the handle portion limit relative sliding movement of the body portion and handle portion. A catheter open at both ends has one end fixed to the handle portion for movement therewith, the opposite end of the catheter having a shape memory tip. A fitting is threadedly connected to an enlarged part of the body portion. A sheath is threadedly connected to the fitting and the catheter is slidable and rotatable within the sheath. An annular channel is provided between the sheath and the catheter, this channel being in fluid communication with a bore in the fitting. The outer end of the sheath has holes therethrough in fluid communication with the channel. An irrigation inflow and aspiration outflow tube is also in fluid communication with the bore in the fitting. A first lock is provided adjacent the fitting for controlling the amount of frictional resistance to lengthwise movement of the catheter relative to the sheath and to lock the catheter in position. A medical device such as an endoscope may be received within the catheter for movement relative thereto. A second lock is supported by the handle portion for locking a medical device in position relative to the catheter.

32 Claims, 5 Drawing Sheets

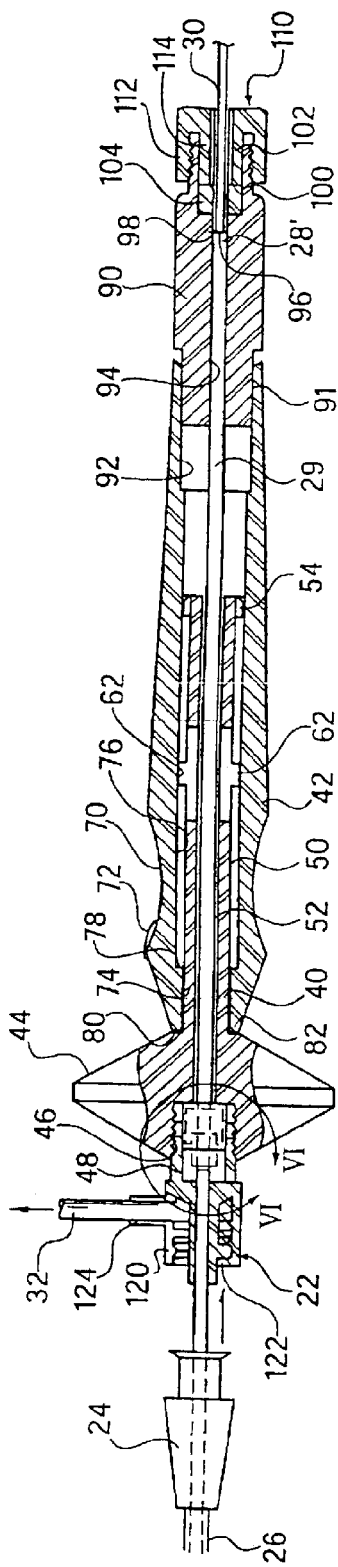
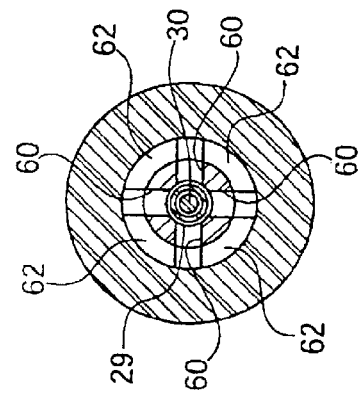
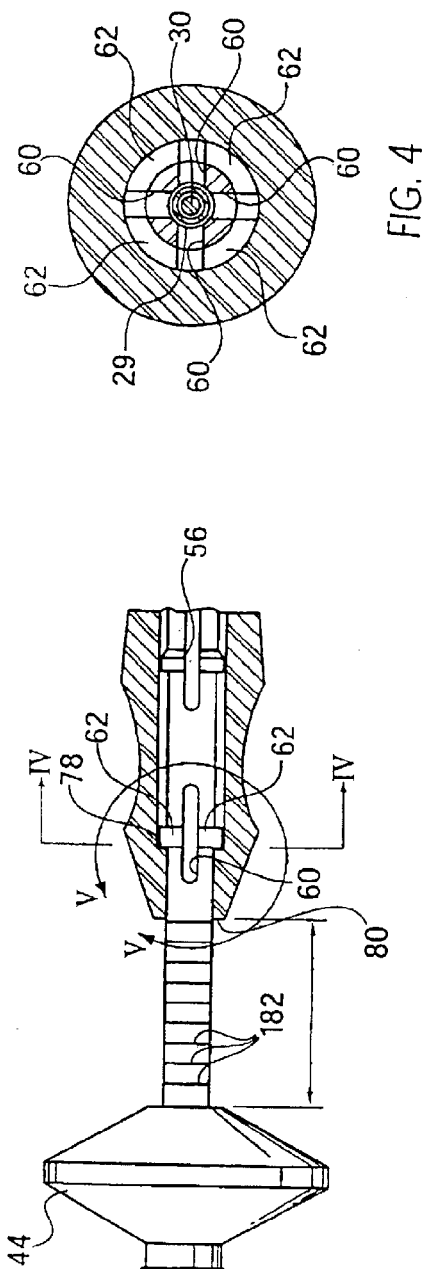

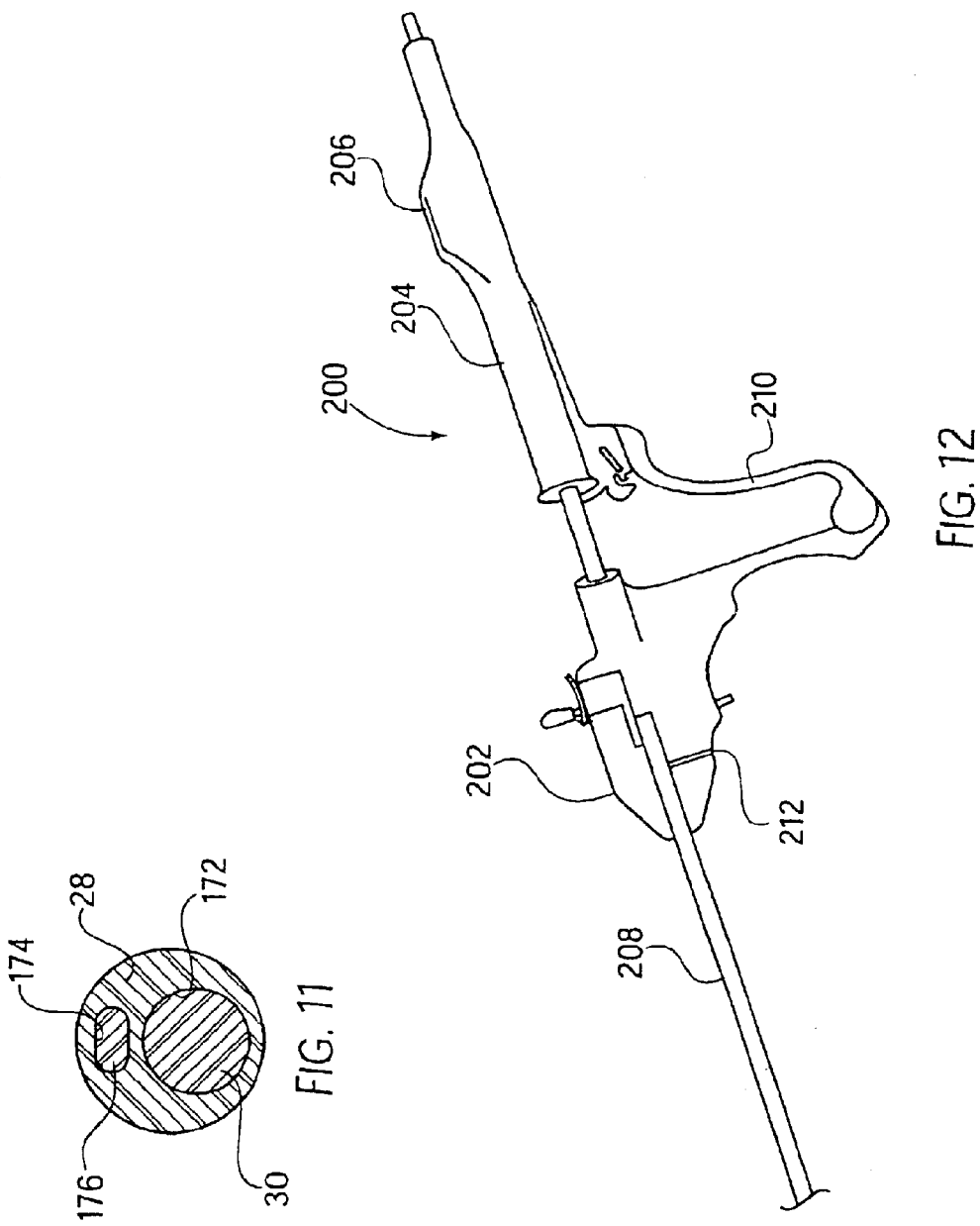

APPARATUS AND METHOD FOR USING A STEERABLE CATHETER DEVICE

RELATED APPLICATIONS

This application is a continuation of application Ser. No. 10/462,182, filed on Jun. 16, 2003, now U.S. Pat. No. 6,679,873, which is a continuation of application Ser. No. 09/665,328, filed Sep. 19, 2000, now U.S. Pat. No. 6,579,279, which claims the benefit of Provisional Application Ser. No. 60/156,051, filed Sep. 24, 1999, the entirety of all these applications are hereby incorporated herein by reference.

BACKGROUND OF THE INVENTION

1. Field of the Invention

The present invention relates to a steerable catheter device, and more particularly to a device useful in minimally invasive surgery, urology, gynecology and hysteroscopy or the like.

2. Description of Related Art

One of the problems associated with procedures such as minimally invasive surgery is the lack of inexpensive small diameter instruments that can be steered into desired locations in the body of a patient. Most of the present available instruments are straight. Steerable instruments are also currently available. However, most of the steerable instruments presently available are complex and heavy. These instruments are generally limited to diameters of 3.6 mm or larger and require complex constructions to accomplish the desired results. At the present time there is no flexible instrument available which enables the instrument to be readily steered within the human body with a minimum of discomfort to the patient while at the same time being small, inexpensive and simple in construction.

Moreover, most presently available instruments require sterilization through the use of cold soak systems—i.e. gluteraldehyde or sterris/sterrad systems. This poses a problem because there have been numerous cases of incomplete sterilization of steerable instruments.

Accordingly, there exists a need for an inexpensive, lightweight, simply constructed instrument that guides and/or steers other instruments. Furthermore, there needs to be a low cost single use instrument to preclude the potential for cross contamination.

SUMMARY OF THE INVENTION

In accordance with this need, the present invention is of lightweight inexpensively constructed steerable catheter device including a handle means which can be held like a pencil. The handle means provides greater sensitivity and tactile feel to the user than is possible with present day devices of this type. Greater sensitivity is provided by the reduction in weight on the handle. Alternatively, the handle means can be shaped as a pistol grip. When shaped as a pistol grip, the probe is constructed so that activation of the handle causes the motion of the probe to be advanced.

In either configuration the activation portion of the steerable catheter can be designed as a reusable piece, since the activation portion is more robust. In this case, the small diameter catheter would be disposable, and provide much simpler delivery to the patient. Reusing portions of the steerable catheter would also lower costs because less material is disposed of with each use.

The handle means supports an elongated outer sheath and an elongated catheter extends through the sheath. The catheter is movable lengthwise of the sheath and is rotatable with respect to the sheath. The outer end of the catheter comprises a memory tip which causes the tip to be disposed at a desired angle to the sheath when the tip is extended a certain distance from the sheath.

The sheath may be substantially rigid, or it may be formed of flexible material. In either case, the catheter is more flexible than the sheath. When the sheath is of flexible construction, complex shapes and bends can be created by rotating the catheter within the sheath. Moreover, with a flexible sheath, the invention may be used not only as a steering instrument but also as a dissection tool.

The instruments and catheters are passed down the lumen of the flexible sheath. Therefore, the inner catheter can be more flexible than would be normally deemed safe because inner catheter is able to secure and derive the wall thickness and strength from the sheath. This construction significantly reduces the potential for breakage.

The handle means includes a body portion which is connected to the sheath and a handle portion which is connected to the catheter. The handle portion is movable with respect to the body portion. These two portions have engageable shoulders formed thereon to limit movement in opposite directions of the catheter relative to the sheath. The sheath may be grasped in one hand of a user to hold the sheath and body portion in position while the other hand manipulates the handle portion to advance or retract the catheter with respect to the sheath and to additionally rotate the catheter with respect to the sheath.

In the pistol grip configuration, the handle is under a spring-loaded force to maintain a backpressure on the handle. The operation may therefore be accomplished in a one handed function. Squeezing the handle causes the insertion of the inner catheter within the outer sheath (as indicated above). A knurled knob on the rotatable portion of the instrument allows the user to adjust the position of the probe by extending a finger and dialing the appropriate position.

Once the tip of the catheter is properly positioned, a suitable medical device can be inserted and advanced through the catheter. For example, an endoscope may be advanced to view tissue more closely, or it can be withdrawn to provide a wider field of view.

The inner lumen can be multi lumen thereby allowing for more than one instrument or device to be inserted (up to the limits of device flexibility). For example, both a small diameter endoscope could be inserted in conjunction with another device; thus delivering both visualization and treatment modalities. Because of the lumens of the inner catheter are adjusted simultaneously (i.e. they are fixed in relative position), the user has the ability to easily move, visualize and deliver the treatment without the additional complication of relative space—relative relationship to each instrument.

A first lock means is supported by the handle means for adjusting the force required to advance and retract the catheter, or to lock the catheter in place relative to the sheath. A second lock means is provided for locking a medical device in position within the catheter. This second lock means can also be adjusted to vary the force required to advance and retract the medical device, if so desired.

The catheter is spaced from the sheath to provide an annular channel there between. The outer end of the sheath has holes formed there through in communication with the annular channel. A fitting is supported by the handle means and has a bore therein in fluid communication with the annular channel. The fitting is also in fluid communication with an irrigation inflow and aspiration outflow tube to allow a constant interchange of fluids within a patient's body cavity or organ to clear the surgical site of debris or blood. The holes in the outer end of the sheath allow irrigation media to be discharged therefrom evenly without a high pressure point. Alternatively, the irrigation system can be used in the delivery of a distension media, a contrast media, or any other desired media.

The relationship of irrigation and aspiration can be altered in that the aspiration can be from the outer tube with the irrigation from the inner tube—the application of the fenestrations on the outer tube preclude the adherence to the tissue wall via the suction creating a high vacuum point.

The steerable catheter of the present invention is inexpensive to manufacture, and its size as it relates to anatomical structures provides a device which is far more comfortable to the patient. When the medical device employed is an endoscope, smaller endoscopes may be interchanged for larger ones as the endoscopes are introduced into smaller diameter channels of the patient. Furthermore, since the endoscope used is a sealed instrument (and requires no working channels because the instrument in which it is inserted maintains the working channels) sterilization thereof is far more a complete and simpler to perform. The used outer sheaths and catheters are simply disposed of and replaced with new items, while the inner scope and other materials may (if applicable) be sterilized.

The system can be used in conjunction with vascular procedure—especially in those instances where there is the use of guidewires. Typically guidewires are used as a leading device—introduced and passed into the area of the vasculature where the larger instrument could either not get to due to size, conformability—or other anatomical issues. To use a guidewire with the present invention, the guidewire is first introduced into the human vasculature. After the guidewire is in place in the body, the guidewire is introduced into the lumen of the instrument—at the active tip. The guidewire is threaded through the catheter until the end of the guidewire exits the rear port of the instrument. The catheter is then introduced into the vasculature, and delivered to the appropriate surgical site by following the guidewire. Because the guidewire is smaller than the instrument, the use of the guidewire allows the instrument tip to reach the desired specific intervention site.

In another aspect of the current invention, the previously described system can be designed so that it mates with an ultrasonic energy source/system. In other words, the ultrasonic probe is introduced into the delivery catheter. In this case, the ultrasonic probe has a wide portion which is semi rigid. This wide portion mates with steerable catheter delivery section. The flexible thin portion of the probe resides within the flexible portion of the delivery system. In operation, the larger more rigid section of the probe does not exhibit vibration patterns. Therefore, the mating of the two surfaces is not problematic (which might be a problem if the large section vibrated). Furthermore, because of this characteristic, the two sections may be "hard mated" together. In the area of the thin section of the ultrasonic probe—it is smaller than the surrounding deflecting catheter and therefore is capable of vibrating in the transverse manner. One suitable ultrasonic probe is described in applicant's co-pending application Ser. No. 09/618,352 which was filed on Jul. 19, 2000, and which is incorporated in its entirety herein.

BRIEF DESCRIPTION OF THE DRAWINGS

FIG. 2 is a longitudinal section through the handle means and adjacent portions of the structure of FIG. 1 showing certain elements in disassembled position;

FIG. 3 is an enlarged view of a portion of the structure shown in FIG. 2 with the handle portions in different relative position to one another;

FIG. 4 is an enlarged section taken along line 4—4 of FIG. 3;

FIG. 11 is an enlarged sectional view taken along line 11—11 of FIG. 10; and

FIG. 12 is a perspective view of another embodiment of the invention.

DESCRIPTION OF THE PREFERRED EMBODIMENTS

Figure 1:
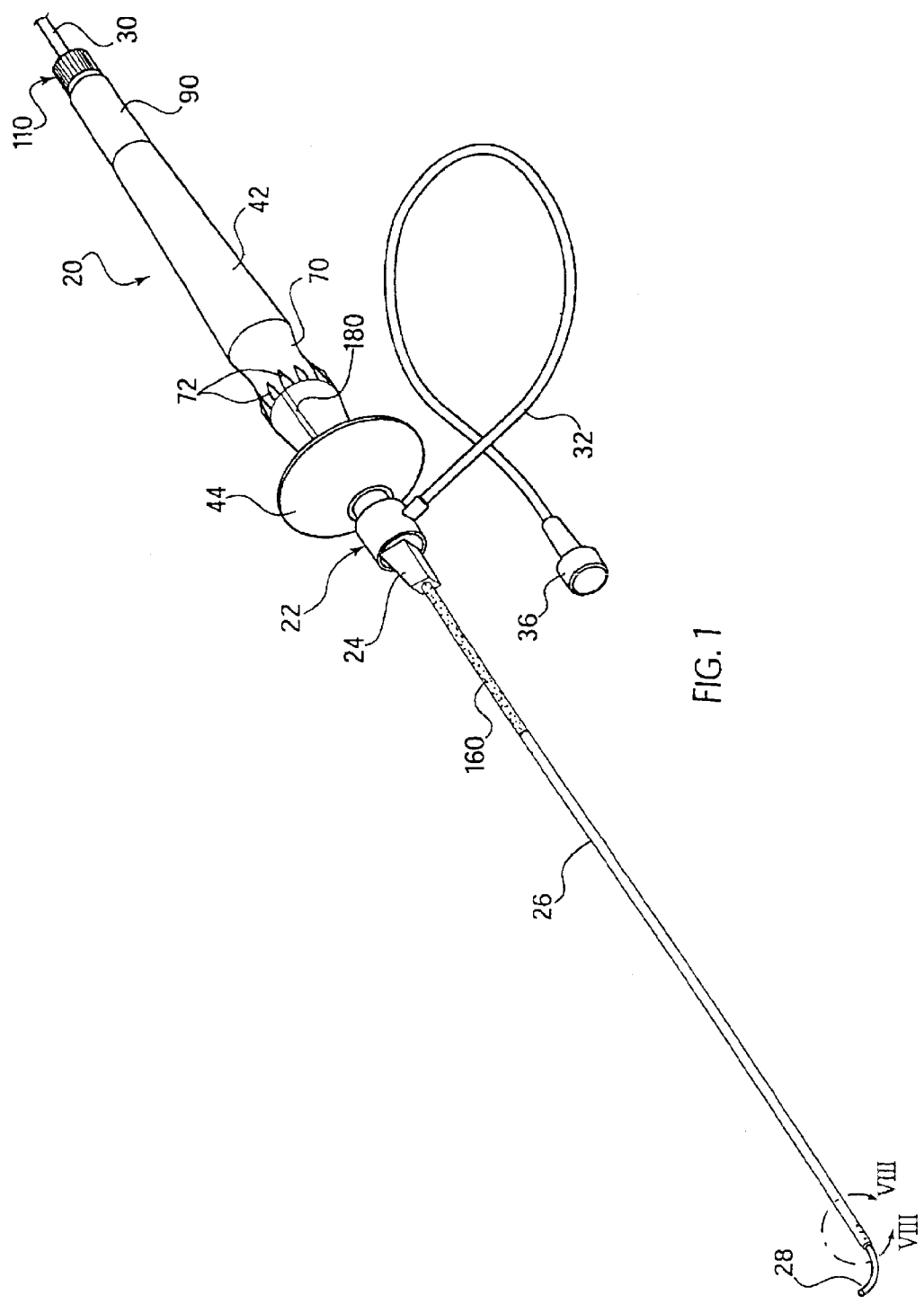
FIG. 1 is a top perspective view of the invention device.

Referring now to the drawings wherein like reference characters designate corresponding parts throughout the several views, the overall device is shown in FIG. 1. A handle means 20 is connected to a fitting 22 which is in turn connected to an attaching means 24 fixed to an outer sheath 26. A catheter tip 28, which is connected to a catheter hereinafter described, extends from the outer end of the sheath, and a medical device 30 such as an endoscope extends through the handle means and is supported within the catheter. The fitting 24 is connected to an irrigation inflow and aspiration outflow tube 32 which has a suitable connector such as a female luer connector at the outer end thereof. The connector is covered by a conventional dust cap 36 when it is not connected to any cooperating equipment.

Referring to FIGS. 2–5, the handle means includes a body portion 40 and a handle portion 42 which is slidably and rotatably supported on the body portion. The body portion and the handle portion are preferably formed of a suitable plastic such as Delrin. The body portion includes an enlarged part 44 which is adapted to be grasped and rotated during use of the device for a purpose hereinafter described. The enlarged part 44 has a threaded bore 46 formed therein which is threadedly connected to a threaded outer surface on a cylindrical portion 48 of the fitting 22.

The body portion 40 includes a cylindrical portion 50 having a bore 52 formed therethrough, portion 50 terminating an outer end having a radially extending annular shoulder 54 thereon. A longitudinally extending slot 56 is formed on the outer end of the portion 50 for providing a resilient end portion. The cylindrical portion 50 has four equally spaced radially extending slots 60 extending inwardly from the outer surface of an intermediate part of the portion 50. The slots are in communication with the bore 52. Arcuate shoulders 62 extend radially outwardly from the portion 50, the shoulders extending between adjacent slot 60. These slots provide a resilient intermediate part of the body portion 40.

The outer surface of the handle portion 42 is configured so as to fit comfortably in the hand of a user and includes a depression 70 for receiving the thumb and forefinger of the user's hand when using the device. As seen in FIG. 1, the forward part of the depression may be provided with a series of spaced protrusions 72 extending around the handle portion to prevent a user's fingers from slipping when rotating the handle portion. Referring to FIG. 2, the handle portion has a first bore 74 formed therein which snugly receives cylindrical part 50 of the body portion. The bore 74 is in communication with a second bore 76 formed within the handle portion. An annular inwardly extending shoulder means 78 is formed between bores 74 and 76.

Figure 5:
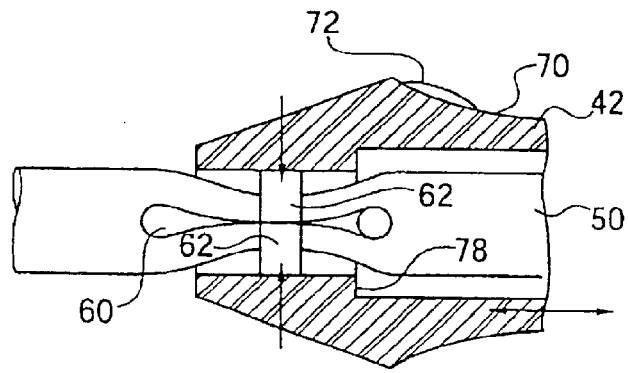
FIG. 5 is an enlarged view of a portion of the structure of FIG. 3 indicated by line 5—5.

It will be noted that when the handle portion 42 is disposed in the position shown in FIG. 2, an annular shoulder means 80 is formed on the forward end of portion 42. The annular shoulder means 80 is in engagement with an outwardly extending shoulder means 82 on the enlarged part 44 of the body portion 40 for limiting movement of the handle portion to the left as seen in this figure. When the handle portion 42 is moved to the right relative to the body portion 40 as seen in FIG. 3, movement of the handle portion to the right is limited by engagement of the shoulder means 78 of the handle portion with the shoulders 62 on the body portion. When assembling the body portion and the handle portion, the slot 56 in the end of the body portion permits the shoulder means 54 to be deflected so that the body means may be inserted through the bore 74 of the handle portion. As seen in FIG. 5, the slots 60 formed in the body means permit the intermediate part of the body portion to be deflected as shown in this figure so that the shoulders 62 may pass through the bore when portions 40 and 42 are assembled.

The handle portion 42 includes an element 90 which also may be formed of any suitable plastic, such as Delrin. The element 90 has a reduced end portion 91 which is received within a bore 92 formed within the handle portion 42. The portions 42 and 91 are adhesively secured in position. The element 90 has a bore 94 formed therethrough which joins with a smaller bore 96 to form an annular shoulder 98 therebetween. A catheter 29 is snugly received within the bore 94, and the rear end 281 of the catheter abuts shoulder 98. The catheter is adhesively secured in place within element 90.

The element 90 also includes an opposite reduced end portion 100 with an external thread formed thereon. A bore 102 is formed within the end portion 100 and has disposed therein a resilient compressible lock member 104 in the form of a conventional silicone gland or the like having a bore formed therethrough which slidably receives a medical device 30 which extends through the catheter. An end cap 110 also formed of a suitable plastic material includes an outer cylindrical portion 112 having an internal thread formed thereon which is in engagement with the external thread formed on end portion 100 of element 90. The end cap also includes an inner cylindrical portion 114 the end surface of which is adapted to engage the lock member 104. When the end cap 110 is threaded to the left as seen in FIG. 2, the end surface of the inner cylindrical portion 114 engages the lock member 104 to compress it in a longitudinal direction. This compression causes the lock member to clamp the medical device 30 to adjust the frictional resistance to lengthwise movement of the medical device or to lock the medical device in position lengthwise of the catheter.

Figure 6:
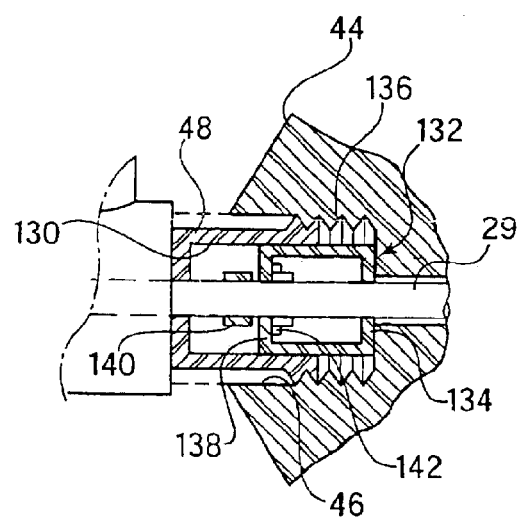
FIG. 6 is an enlarged view of a portion of the structure of FIG. 2 indicated by line 6—6.

The fitting 22 includes a cylindrical portion 120 having an internally threaded bore 122 therein. The threaded bore 122 is in communication with a side port 124. The side port 124 is connected to and is in fluid communication with the tube 32. As seen in FIG. 6, a bore 130 is formed within the cylindrical portion 48 of the fitting. A resilient compressible lock member 132 in the form of a conventional lip seal may be formed of the same material as lock member 104 previously described. The lip seal includes a wall 134 having a hole therein for slidably receiving the catheter 29. The wall 134 joins with a cylindrical wall 136 which joins with a radial wall 138 which joins with a lip 140 defining a bore therethrough for slidably receiving the catheter. A conventional o-ring 142 is disposed around the lip 140 for retaining it in sealing relationship with the catheter 29.

When the enlarged part 44 of the body portion is rotated to thread the body portion to the left as seen in FIG. 6, the lock member 132 is compressed and tightens down on the catheter extending therethrough. The lock member may be compressed to varying degrees to adjust the resistance to longitudinal movement of the catheter and handle portion relative to the sheath and body portion, or it may be compressed to such extent that the catheter is locked against longitudinal movement relative to the sheath. This locking action can be accomplished in an infinite number of positions between the two spaced limits of relative movement in opposite directions of the catheter relative to the sheath.

Figure 7:
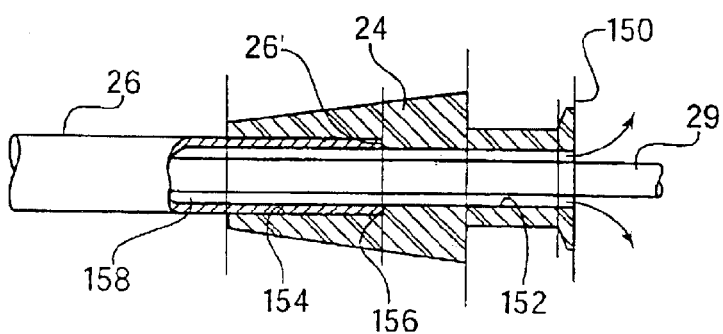
FIG. 7 is an enlarged cross-section of a portion of the structure shown in FIG. 2.

As seen in FIG. 7, the attaching means 24 comprises a conventional luer fitting having thread means 150 at one end thereon. The attaching means 24 is threaded into the internally threaded bore 122 of the fitting 22. A first bore 152 is formed through the means 24 and is of greater diameter than the outer diameter of the catheter 29 which passes therethrough to allow fluid to pass through the bore 152 and around the catheter. A bore 154 of greater diameter than the bore 152 is provided within the attaching means 24, and an annular shoulder 156 is defined between the two bores. The inner end 261 of the sheath 26 fits within the bore 154 and is adhesively secured thereto with the inner end surface abutting shoulder 156. The outer surface of the catheter is spaced from the inner surface of the sheath to form an annular channel 158 therebetween.

It is noted that the outer surface of the sheath is bead-blasted to provide a frosted surface indicated at 160 on FIG. 1. This surface provides a non-slip portion to ensure that a user having wet gloves on his hand will have a secure grip on the device. In normal use, a user will support the device by gripping surface 160 in one hand while manipulating the handle portion with the other hand.

Figure 8:
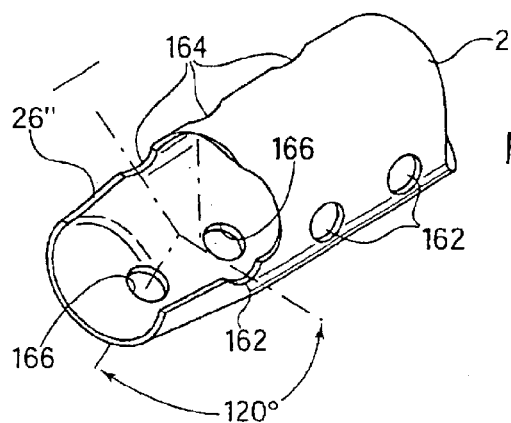
FIG. 8 in an enlarged view partly broken away of a portion of the structure of FIG. 1 indicated by line 8—8.
Figure 10:
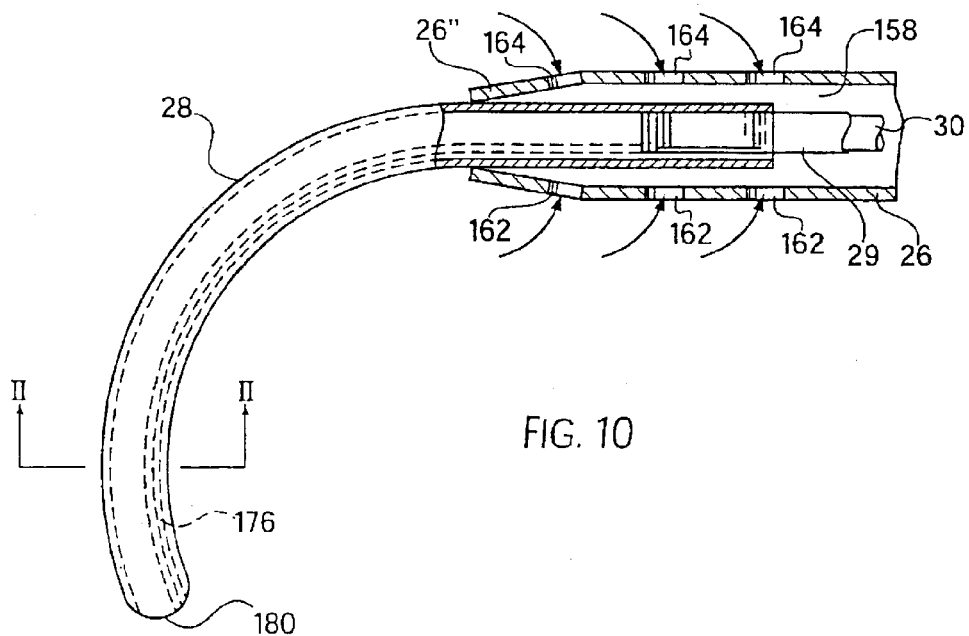
FIG. 10 is an enlarged view partly in section of the structure shown in FIG. 9.

As seen in FIGS. 8 and 10, the outer end of the sheath 26 is tapered inwardly at 26. Three rows of holes 162, 164 and 166 extend lengthwise of the sheath. There are three holes in each row and the rows are equally spaced from one another about the circumference of the sheath. The arrows in FIG. 10 indicate the direction in which fluid may flow into the fluid flow channel 158 between the sheath 26 and the catheter 28 thence through the channel 158, the bore 152 of the attaching means 24 and thence through the tube 32 when the tube is connected to a device providing aspiration outflow from the device. When irrigation fluid is to be transmitted to the end of the sheath, fluid will flow in the opposite direction from that indicated in FIG. 10 and will be discharged through the holes 162, 164 and 166. The symmetric arrangement of the holes allows irrigation or distention media to be discharged from the device evenly without a high pressure point. A constant interchange of fluids within a patient's body cavity organ can be accomplished while using the device.

As seen in FIG. 10, the catheter tip 28 and the catheter 29 are separate components which are secured to one another.

The outer end of the catheter 28 is provided with grooves 170 which receive a suitable adhesive material to fix the catheter to the catheter tip. The tip 29 is a shape memory tip and includes a lumen 172 which receives an endoscope 30 (as seen in FIG. 11). A second lumen 174 receives an internal stiffening wire 176 such as stainless steel or other alloy which causes the tip to bend at an angle to the longitudinal axis of the device in a well-known manner.

Figure 9:
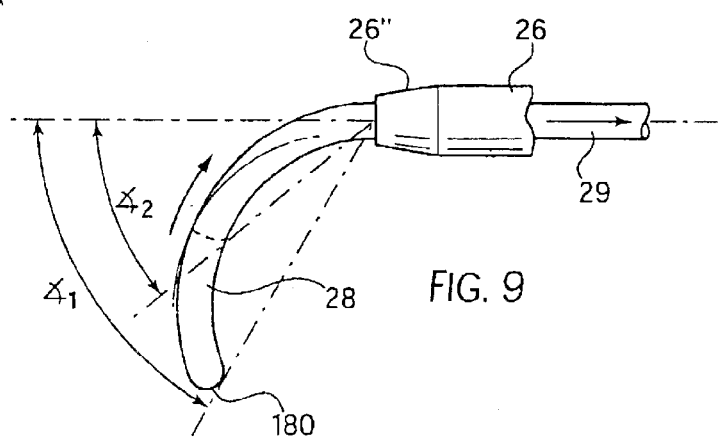
FIG. 9 is a view partly broken away showing the outer end of the device shown in FIG. 1.

As shown in FIGS. 9 and 10, the end of the tip extends at substantially 90 degrees to the longitudinal axis of the device when the catheter is fully extended from the sheath. It should be understood that the catheter can also be withdrawn so as to be entirely contained within the sheath wherein the tip is substantially aligned with the longitudinal axis of the catheter. As seen in FIG. 9, as the tip is withdrawn into the sheath from its fully extended position, the angle of the tip relative to the longitudinal axis can be varied infinitely between about 90 degrees and 0 degrees.

The outer end of the tip 29 is rounded as indicated at 180 to provide increased comfort to a patient. Suitable radio-paque markings may be provided on the tip 28 to indicate the location and positioning of the catheter tip when radiographs are taken. The entire device may be radiolucent with the exception of the tip of the catheter. The inner catheter may have a plurality of lumens which would allow the use of small flexible instruments to be introduced and delivered to the surgical site alongside an endoscope to provide direct visualization.

As seen in FIG. 1, a suitable mark 180 is provided on the handle portion 42. The mark 180 is aligned with the catheter tip 28 when it is extended from the sheath so that a user can tell what the angular relationship of the tip is by observing the position of mark 180. As seen in FIG. 3, the body portion 40 has external markings 182 thereon which can be aligned with the shoulder 80 on the end of the body portion to indicate the distance the catheter tip has been extended beyond the end of the sheath. The amount of extension of the catheter tip determines the angularity of the tip to the sheath, and therefore the markings 182 provide an indication of the angularity of the tip to the sheath and the longitudinal axis of the device.

The sheath 26 may be formed of metal to provide a rigid sheath, or it may be formed of a flexible material to allow it to be inserted into tortuous and difficult application areas. In either case, the catheter is formed of a material which is more flexible than the material of the sheath.

FIG. 12 shows another embodiment of the handle means 200 of the present invention. In this embodiment, the handle means is pistol-shaped, so that a user may comfortably grasp the hand means with one hand. The handle means has a handle portion 202 and a body portion 204. The body portion 204 is slidably and rotatably supported on the handle portion 204. The body portion 204 includes an enlarged part 206 which is adapted to be grasped and rotated during use of the device. The handle portion 202 is connected to a retracting trigger 210, which is pivoted on the body portion 204. A spring in the handle portion 202 provides a back pressure to the retracting trigger 210. The handle portion 202 has a bore for receiving a sheath 208, and may include an aspiration fitting or luer 212. The fitting is configured for connection with a flexible tube which is in turn connected to a source of reduced pressure. The remaining portions of the handle portion 202 and device are the same as described with respect to the other embodiment of the handle. When the retracting trigger 210 is squeezed, a catheter within the sheath is withdrawn or extended. In all other respects, the operation of the device is the same as described with respect to the embodiment with the pencil shaped handle.

The invention has been described with reference to a preferred embodiment. Obviously, various modifications, alterations and other embodiments will occur to others upon reading and understanding this specification. It is our intention on to include all such modifications, alterations come within the scope thereof. Any modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. A steerable catheter device comprising:

a sheath engaging a body portion of a handle, the sheath having an outer end and an inner end;

a fitting supported by the handle and engaging the sheath;

a flexible catheter engaging the handle and extending through the sheath, the flexible catheter having opposite open ends with a distal end of the flexible catheter engaging a shape memory catheter tip;

a medical device inserted within the flexible catheter; and a first lock comprising a resilient compressible lock member, the first lock supported by the handle for adjusting a force required for longitudinal movement of the flexible catheter relative to the sheath and for locking the flexible catheter relative to sheath along a longitudinal axis of the sheath.

2. The steerable catheter device of claim 1 wherein the first lock comprises a portion of the handle threadably engaging the fitting.

3. The steerable catheter device of claim 1 wherein the first lock locks the flexible catheter relative to the sheath in a plurality of locations between a first limit of the handle and a second limit of the handle.

4. The steerable catheter device of claim 1 wherein the first lock controls a frictional resistance to longitudinal movement of the flexible catheter relative to the sheath.

5. The steerable catheter device of claim 1 wherein the fitting is engaged to an irrigation inflow tube.

6. The steerable catheter device of claim 1 wherein the fitting is engaged to an aspiration outflow tube.

7. The steerable catheter device of claim 1 wherein the fitting is engaged to an irrigation inflow tube and an aspiration outflow tube.

8. The steerable catheter device of claim 1 wherein the flexible catheter is disposable.

9. The steerable catheter device of claim 1 wherein a distal end of the shape memory catheter tip is rounded.

10. The steerable catheter device of claim 1 wherein the shape memory catheter tip comprises a plurality of radiopaque markings.

11. The steerable catheter device of claim 1 further comprising a second lock supported by the handle for adjusting the force required for longitudinal movement of the medical device relative to the flexible catheter and for locking the medical device relative to the flexible catheter.

12. The steerable catheter device of claim 11 wherein the second lock comprises a resilient compressible lock member.

13. The steerable catheter device of claim 11 wherein the second lock comprises an end cap threadably mounted on the handle.

14. A steerable catheter device comprising:

a sheath having a plurality of holes at an outer end of the sheath for discharging an irrigation media;

a handle having a body portion engaging the sheath for supporting the sheath;

a catheter extending through the sheath creating an annular channel between the catheter and the sheath, the catheter engaging the handle;

a fitting engaging the handle at a proximal end of the fitting;

a medical device inserted within the catheter;

a first lock supported by the handle for controlling longitudinal movement of the catheter relative to the sheath;

a second lock supported by the handle for controlling longitudinal movement of the medical device relative to the catheter, the second lock comprising a resilient compressible lock member.

15. The steerable catheter device of claim 14 wherein a shape memory catheter tip engages a distal end of the catheter.

16. The steerable catheter device of claim 15 wherein the shape memory catheter tip extends from a distal end of the sheath.

17. The steerable catheter device of claim 14 wherein the fitting engages an irrigation inflow tube and an aspiration outflow tube.

18. The steerable catheter device of claim 14 wherein the body portion of the handle is adapted to be grasped and rotated to lock the first lock.

19. The steerable catheter device of claim 14 wherein the first lock adjusts a force required for longitudinal movement of the catheter relative to the sheath.

20. The steerable catheter device of claim 14 wherein the first lock controls a frictional resistance to longitudinal movement of the catheter relative to the sheath.

21. The steerable catheter device of claim 14 wherein the second lock comprises an end cap threadably engaging the handle.

22. The steerable catheter device of claim 15 wherein the second lock adjusts a force required for longitudinal movement of the medical device relative to the catheter.

23. The steerable catheter device of claim 15 wherein the second lock controls a frictional resistance to longitudinal movement of the medical device relative to the catheter.

24. A method of delivering a medical device in a vasculature of a body comprising:

inserting a guidewire in the vasculature;

moving a steerable catheter device over the guidewire, the steerable catheter device having a handle, a sheath supported by the handle and a flexible catheter extending through the sheath;

moving the flexible catheter within the sheath to a treatment site;

locking the flexible catheter relative to the sheath with a first lock;

inserting the medical device through a proximal end of the flexible catheter at a proximal end of the steerable catheter device;

advancing the medical device to the treatment site;

locking the medical device relative to the flexible catheter with a second lock; and removing the guidewire from the vasculature of the body.

25. The method of claim 24 further comprising inserting the flexible catheter of the steerable catheter device over the guidewire.

26. The method of claim 24 further comprising engaging a shape memory catheter tip to a distal end of the flexible catheter.

27. The method of claim 24 further comprising squeezing a trigger portion of the handle to advance the flexible catheter relative to the sheath.

28. The method of claim 24 further comprising rotating a body portion of the handle to compress a first resilient compressible lock member of the first lock on the flexible catheter to lock the flexible catheter relative to the sheath.

29. The method of claim 24 further comprising rotating an end cap of the handle to compress a second resilient compressible lock member of the second lock on the medical device to lock the medical device relative to the flexible catheter.

30. The method of claim 24 further comprising irrigating the treatment site with an irrigation tube delivering an irrigation medium through a plurality of holes in the sheath.

31. The method of claim 24 further comprising aspirating debris from the treatment site with an aspiration tube.

32. The method of claim 24 further comprising engaging the handle to the sheath with a fitting.

* * * * *

UNITED STATES PATENT AND TRADEMARK OFFICE
CERTIFICATE OF CORRECTION

PATENT NO. : 6,802,835 B2
DATED : October 12, 2004
INVENTOR(S) : Rabiner et al.

It is certified that error appears in the above-identified patent and that said Letters Patent is hereby corrected as shown below:

Column 9,
Lines 41 and 44, delete "15" and insert -- 14 --.

Signed and Sealed this

First Day of February, 2005

JON W. DUDAS
*Director of the United States Patent and Trademark Office*